United States Patent [19]

Socci et al.

[11] Patent Number: 5,863,523
[45] Date of Patent: Jan. 26, 1999

[54] NAIL ENAMEL COMPOSITION

[75] Inventors: Robert L. Socci, Cedar Grove, N.J.; Anatoly Ismailer, Roslyn Heights, N.Y.

[73] Assignee: Kirker Enterprises, Inc., Paterson, N.J.

[21] Appl. No.: 762,928

[22] Filed: Dec. 10, 1996

[51] Int. Cl.$^6$ .............................. A61K 6/00; A61K 7/00; A61K 7/04
[52] U.S. Cl. .............................. 424/61; 424/401
[58] Field of Search .......................... 424/61, 401; 106/5; 260/1.6; 523/448

[56] References Cited

U.S. PATENT DOCUMENTS

| | | | |
|---|---|---|---|
| 2,195,971 | 4/1940 | Peter | 167/85 |
| 3,864,294 | 2/1975 | Busch, Jr. | 260/28.5 A |
| 4,097,440 | 6/1978 | Maximovich et al. | 260/16 |
| 4,301,046 | 11/1981 | Schlossman | 260/16 |
| 4,402,935 | 9/1983 | Gordon et al. | 424/61 |
| 4,421,881 | 12/1983 | Benkendorf et al. | 524/24 |
| 4,712,571 | 12/1987 | Remz et al. | 132/88.7 |
| 4,820,509 | 4/1989 | Yamazaki et al. | 424/61 |
| 4,822,423 | 4/1989 | Soyama et al. | 106/5 |
| 4,897,261 | 1/1990 | Yamazaki et al. | 424/61 |
| 5,001,175 | 3/1991 | Skora | 523/448 |
| 5,118,495 | 6/1992 | Nafziger et al. | 424/61 |
| 5,133,966 | 7/1992 | Khamis | 424/401 |
| 5,145,671 | 9/1992 | Castrogiovanni et al. | 424/61 |
| 5,206,011 | 4/1993 | Pappas et al. | 424/61 |
| 5,290,543 | 3/1994 | Ounanian et al. | 424/61 |
| 5,424,061 | 6/1995 | Pappas et al. | 424/61 |
| 5,435,994 | 7/1995 | Valenty | 424/61 |
| 5,470,562 | 11/1995 | Khamis | 424/401 |

OTHER PUBLICATIONS

Kodaflex TXIB Product Brochure, undated.

*Primary Examiner*—Thurman K. Page
*Assistant Examiner*—Sharon Howard
*Attorney, Agent, or Firm*—Lerner, David, Littenberg, Krumholz & Mentlik

[57] ABSTRACT

Nail enamel compositions include a primary film forming polymer, a secondary film forming resin, a solvent and a plasticizer. The secondary film forming resin is present in the composition in an amount greater than the primary film forming polymer. The resulting nail enamel composition has improved wear characteristics and properties which are suitable for use as base coats, color coats, clear coats and protective top coats.

40 Claims, No Drawings

NAIL ENAMEL COMPOSITION

FIELD OF THE INVENTION

The present invention relates in general to nail enamel compositions, and more particularly, to such compositions which are suitable for use as base coats, color coats, clear coats and protective top coats for coating natural and synthetic nails. Still more particularly, the present invention relates to nail enamel compositions which exhibit improved wear characteristics and properties by virtue of the presence of one or more secondary film forming resins in an amount greater than the primary film forming polymer.

BACKGROUND OF THE INVENTION

Nail enamel compositions include a class of nail care products regularly used by women as part of their beauty care routine. These nail care products are available in a multitude of product formulations, from clears to infinite colors. Typically, clear nail enamel compositions include a primary film forming polymer, a secondary film forming resin, a plasticizer and one or more solvents. In the case of a color nail enamel composition, the product will also include a thixotropic compound as a suspending agent and one or more pigments, or in the alternative, an organic coloring polymer may be used. In addition to these components, a number of optional and proprietary components are often included such as UV light absorbers, moisturizers, stabilizers, fragrances and the like.

Despite the diverse formulation differences between known nail enamel compositions, the required performance expectations are frequently the same, for example, smooth application, rapid dry time, scratch resistance, detergent and oil resistance, lustrous appearance and, often most importantly, wear and peel resistance. Many efforts to date have been made in order to maximize wear and peel resistance of nail enamel compositions through the use of various components and additives. For example, see Soyama et al., U.S. Pat. No. 4,822,423 which uses 0.1% to 2.5% mica in the form of a leaf; Yamazaki, et al., U.S. Pat. No. 4,820,509 which uses 1% to 4% of sucrose benzoate in combination with toluene sulfonamide formaldehyde resins. However, there is still the need for further improvements in nail enamel compositions. Accordingly, the present invention broadly discloses nail enamel compositions having improved peel and wear characteristics.

SUMMARY OF THE INVENTION

The broad objects of the present invention are to provide nail enamel compositions which are suitable for use as base coats, color coats, clear coats and protective top coats while maintaining the desirable characteristics of the nail enamel compositions.

Another object of the present invention is to provide nail enamel compositions having a higher secondary film forming resin content compared to the primary film forming polymer.

Another object of the present invention is to provide nail enamel compositions having improved peel and wear resistance.

Broadly, in accordance with the present invention, there is disclosed nail enamel compositions which include a secondary film forming resin present in an amount greater than the primary film forming polymer. The resulting nail enamel compositions evidence good gloss and wear and peel resistance, while at the same time, being safe to use with frequent applications.

In accordance with one embodiment of the present invention there is described a nail enamel composition consisting essentially of a film forming polymer, a film forming resin present in an amount greater than an amount of the film forming polymer, a solvent and a plasticizer.

In accordance with another embodiment of the present invention there is described a nail enamel composition comprising a film forming polymer, a film forming resin present in an amount greater than an amount of the film forming polymer, a solvent and a plasticizer, wherein the composition is free of mica in the form of a leaf and hydrocarbon based solvents.

In accordance with another embodiment of the present invention there is described a nail enamel composition comprising a film forming polymer, a film forming resin selected from the group consisting of polyester resins, epoxy resins and mixtures thereof, the film forming resin present in an amount greater than an amount of the film forming polymer, a solvent and a plasticizer.

With an endless list of possible compounds which are functionally suitable for use in a nail enamel composition, safety to the user in general, and to the fingernail in particular, is also a very important consideration. Heretofore, various techniques have been disclosed with respect to compositions of resins and solvents for improving, in particular, the safety factor against damage to the fingernail while, at the same time, maintaining the desirable properties of the nail enamel composition, e.g., good peel and wear resistance. In this regard, there is known a number of nail enamel components which are desirable of being removed from the formulation. For example, nail enamel compositions traditionally included a phthalate compound such as dibutyl phthalate as a plasticizer; an adhesion promoter or film forming resin such as a polymeric compound formed by condensation polymerization of formaldehyde or other aldehydes, typically an aromatic sulfonamide-aldehyde condensation resin such as o, p-toluene sulfonamide formaldehyde resin; and toluene as a diluent.

It is desirable that nail enamel compositions eliminate or reduced the amounts of phthalates, aldehydes (e.g., formaldehyde) condensation products and toluene in order to alleviate concerns that some wearers may be sensitized to the aforementioned components. In addition, the use of toluene in nail enamel compositions has been severely restricted in California under Proposition 65. However, attempts to formulate nail enamel compositions without the aforementioned components have uncovered difficulties because of the requirement to maintain the properties required of these compositions, such as long wear, high gloss, rapid dry time, resistance to chipping and peeling, and compatibility with other nail enamel components. In addition, these desired properties of nail enamel compositions are highly sensitive to changes in their components and to changes in the amounts of these components. Therefore, there is still the need for nail enamel compositions having improved wear and peel resistance and which exhibit satisfactory properties, as well as containing little or no undesirable components such as phthalates, aldehyde condensation products and/or toluene.

In accordance with another embodiment of the present invention there is described a toluene formaldehyde free nail enamel composition consisting essentially of about 5 to 20% by weight nitrocellulose, about 10 to 25% by weight of one or more formaldehyde free film forming resins, the film forming resins present in an amount greater than the amount of the nitrocellulose, a solvent and a plasticizer, and optionally a thixotropic agent and at least one pigment.

These and other objects, features and advantages of the present invention, as well as details of the preferred embodiments thereof, will be more further understood from the following detailed description.

DETAILED DESCRIPTION OF THE PREFERRED EMBODIMENTS

Nail enamel compositions of the present invention for coating a natural or synthetic nail broadly include the ingredients of a primary film forming polymer, a secondary film forming resin, a plasticizer and a solvent. The resulting composition will provide a clear nail enamel. Where a colored nail enamel composition is desired, a thixotropic suspending agent and one or more pigments, or organic coloring polymers may be included in the composition. In addition to the above components, the nail enamel compositions according the present invention may further include one or more additional ingredients, for example, UV light absorbers, stabilizer, fragrances, moisturizers and the like. Nail enamel compositions of these components are useful in a wide variety of cosmetic applications such as base coats, color coats, clear coats and protective top coats.

The nail enamel compositions of the present invention contain one or more primary film forming polymers, for example, cellulose acetate, cellulose acetate butyrate, ethyl cellulose, vinyl polymers, nitrocellulose, as well as methacrylate and acrylate type polymers. The preferred primary film forming polymer for use in the present invention is nitrocellulose which provides an unusual combination of properties of toughness, durability, solubility and solvent release. Examples of nitrocellulose are the so called nitrocellulose RS ⅛ sec. and ¼ sec.; nitrocellulose ½ sec.; and nitrocellulose RS 5–6 sec. and 60–80 sec., which have higher viscosities than the earlier grades. The term "RS" refers to the brand of nitrocellulose with a nitrogen content of about 11.2–12.8% with solubility in esters, ketones and glycol ethers manufactured by Hercules, Inc. The terms ⅛ sec., ¼ sec., ½ sec., 5–6 sec., etc. represent viscosity and refer to the time it takes for a ball to fall to a given depth in the material. Nitrocellulose is typically supplied in 70% concentrations, wet with 30% ethyl or isopropyl alcohol. As used in the present application, the percentage of nitrocellulose in a given composition will be on a dry basis.

The use of too small an amount of nitrocellulose tends to result in the coated films being easily damaged. On the other hand, the use of too large an amount of nitrocellulose can result in the coated film being too hard and inflexible, which easily causes undesirable peeling and hence poor wear resistance. Nail enamel compositions of the present invention include primary film forming polymers and combinations thereof in an amount ranging from about 5 to 20% by weight, and more preferably in the range of about 6 to 9% by weight.

In addition to the primary film forming polymer, the nail enamel compositions of the present invention include an amount of one or more secondary film forming resins effective to strengthen the primary film forming polymer and to provide the nail enamel coating with acceptable gloss and adhesion characteristics. Exemplary secondary film forming resins which may be used in the present invention include, for example, drying and non-drying alkyd resins, polyvinyl resins for example polyvinyl acetate, polyester resins, acrylic polymers and copolymers, maleic modified glycerol esters of rosin, and toluene sulfonamide/epoxy resins, e.g., tosylamide epoxy resin.

It is also within the scope of nail enamel compositions of the present invention to include, if desired, aldehyde condensation products such as arylsulfonamide formaldehyde resins, specifically toluene sulfonamide formaldehyde resin which is a condensation product of formaldehyde and toluene sulfonamide. These secondary film forming resins are added to the nail enamel compositions of the present invention to strengthen and add acceptable wear characteristics to the primary film forming polymer.

The preferred nail enamel compositions of the present invention include as the secondary film forming resins polyester resins, epoxy resins such as tosylamide epoxy resins and mixtures thereof. The amount of secondary film forming resin is present in an amount greater than the amount of the primary film forming polymer. The resulting nail enamel compositions having a higher secondary film forming resin content result in the nail enamel coating possessing superior gloss and wear characteristics over conventional nail enamel compositions. In addition, these compositions retain the desirable properties and characteristics required of nail enamel compositions. The amount of secondary film forming resin ranges from about 10 to 25% by weight of the composition, and preferably about 10 to 15% by weight of the composition.

In addition to the primary film forming polymer and secondary film forming resin, the nail enamel compositions according to the present invention also include at least one plasticizer to soften and plasticize the primary film forming polymer. The plasticizer may be in either liquid or solid form, as well as combinations thereof. The nail enamel compositions may include one or more of the known plasticizers which are suitable for use in nail enamel compositions. Examples of such known plasticizers include tricresyl phosphate, dibutyl tartrate, benzyl benzoate, tributyl phosphate, butyl acetyl ricinoleate, butyl glycolate, butyl stearate, triphenyl phosphate, triethyl citrate, camphor, castor oil, esters of citric, stearate, phalic, oleic, phosphate, butyric and benzoic acid, glyceryl triacetate and glyceryl triprionate and mixtures thereof.

Another useful plasticizer which has heretofore been unknown for use in nail enamel compositions includes compounds of:

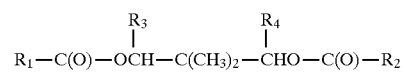

wherein $R_1$ and $R_2$ are the same or different and represent linear or branched alkyl groups containing from one to 18 carbon atoms, and $R_3$ and $R_4$ are the same or different and represent linear or branched alkyl groups containing from one to five carbon atoms, provided that one of $R_3$ or $R_4$ may be hydrogen. These plasticizers include compounds of 2, 2, 4-trimethyl-1, 3-pentanediol and derivatives thereof, such as its mono- and diisobutyrate esters, and most preferably 2, 2, 4-trimethyl-1, 3-pentanediol diisobutyrate which is disclosed in Applicants' co-pending application. The nail enamel compositions of the present invention also contemplate, if desired, the use of phthalate type plasticizers either alone or in combination with the aforementioned plasticizers.

Plasticizers included in the compositions of the present invention are in amounts sufficient to provide acceptable flexibility to the nail enamel film on the human or synthetic nail surface. In this regard, the amount of plasticizer for use in the nail enamel compositions of the present invention range from about 3 to 10% by weight, and preferably about 4 to 8% by weight.

The nail enamel compositions of the present invention include one or more solvents such as those generally used in conventional nail enamel compositions. Examples of these solvents include ethyl acetate, methyl acetate, ethanol, isopropanol, propyl acetate, n-butanol, xylene, aromatic (containing phenyl groups), amyl acetate, ethers, ketones, alkanes for example, pentane, cyclopentane, hexane, heptane, cyclohexane, cyclic ethers for example, tetrahydrofuran and 1,4-dioxane, cellosolve, butyl cellosolve acetate, cellosolve acetate, methyl cellosolve acetate, butyl cellosolve, ethyl cellosolve, phenylated solvents for example, xylene, esters of acetic acid for example, methyl acetate, ethyl acetate, n-butyl acetate, chlorinated hydrocarbons for example, methylene chloride, chloroform and methylchloroform. It is also contemplated that toluene, if desired, can be included as a solvent or diluent for use in a nail enamel composition in accordance with the compositions of the present invention. The aforementioned solvents can be used alone or in mixtures thereof. In general, the amount of solvent used in the compositions of the present invention range from about 55 to 80% by weight, and preferably about 60 to 75% by weight.

In color compositions according to the present invention, one or more pigments and a thixotropic agent are also added. One or more known organic colorants may also be added to these compositions. Pigments are added to the composition to provide cosmetically acceptable shades and to pacify the films. Pigments for use in the present invention may include any of those pigments which are generally known for use in nail enamel compositions. For example, these pigments can include cosmetic grade or purified titanium dioxide, yellow and red iron oxides, bismuth oxychloride, iron blue, iron black, mica particles, ultramarine blue, D&C Red #7, chromide oxide greens, carbon black and lampblack. Other pigments which may be used in compositions according to the present invention may include the Lake pigments, for example, D&C Red #6 barium Lake and D&C Red #7 calcium Lake.

In addition to the above named pigments, there may also be included titanated micas, polethylene teraphalates and pearl essence which is a suspension of crystalline guanine in nitrocellulose and solvents, as well as other additives which will affect the appearance of the pigment. Although the amount of pigment in the compositions of the present invention will vary as a function of the type of pigment and other components included in the composition, in general, pigments can be included in the amount up to about 15% by weight, and preferably in the amount up to from about 1 to 4% by weight.

When pigments are included in compositions according to the present invention, it is useful to include a thixotropic agent for enhancing the suspension of the pigments in the other components of the composition. Although a number of thixotropic agents which are generally used in conventional nail enamel compositions may be used to produce compositions according to the present invention, preferred thixotropic agents include the thixotropic clays, especially stearalkonium hectorite, stearalkonium bentonite and mixtures thereof. The thixotropic agent is present in the compositions of the present invention in amounts sufficient to produce a gel, preferably a colloidal gel. In general, the thixotropic agent is included in the amount ranging from about 0.5 to 3% by weight, and preferably in the amount ranging from about 0.7 to 1.5% by weight.

In addition to the above described components, the compositions of the present invention may also include additional additives including stabilizers, UV light absorbers, fragrances, moisturizers and medicants, depending on the intended result. These components are well known in the art and may be included in amounts well within the teachings of the prior art.

The nail enamel compositions in accordance with the present invention can be manufactured by thoroughly and intimately mixing together all the components in the amounts described in accordance with the present invention. Examples of satisfactory equipment and how to use then are readily apparent to one of ordinary skill in the nail enamel art.

The following examples are provided to illustrate the nail enamel compositions of the present invention and should not be construed to limit the scope of the invention in any way.

EXAMPLE 1

|  | WT. % |  |
| --- | --- | --- |
| nitrocellulose ¼ sec. | 3.8 | (dry) |
| nitrocellulose 5–6 sec. | 4.2 | (dry) |
| toluenesulfonamide formaldehyde resin | 12.8 |  |
| triphenyl phosphate | 6.00 |  |
| ethyl acetate | 30.43 |  |
| butyl acetate | 25.10 |  |
| isopropyl alcohol | 14.56 |  |
| 2,2,4-trimethyl-1,3-pentanediol diisobutyrate | 1.0 |  |
| stearalkonium bentonite | 1.05 |  |
| pigment | 1.06 |  |
|  | 100.00 |  |

EXAMPLE 2

|  | WT. % |  |
| --- | --- | --- |
| nitrocellulose ¼ sec. | 3.7 | (dry) |
| nitrocellulose 5–6 sec. | 4.2 | (dry) |
| toluenesulfonamide epoxy resin | 12.00 |  |
| triphenyl phosphate | 4.50 |  |
| isopropyl alcohol | 13.60 |  |
| ethyl acetate | 32.35 |  |
| butyl acetate | 25.55 |  |
| 2,2,4-trimethyl-1,3-pentanediol diisobutyrate | 2.0 |  |
| stearalkonium bentonite | .98 |  |
| pigment | 1.12 |  |
|  | 100.00 |  |

The following examples are provided to broadly illustrate suspension bases for color nail enamel compositions.

EXAMPLE 3

|  | WT. % |  |
| --- | --- | --- |
| polyester resin | 5.60 |  |
| tosylamide epoxy resin | 4.96 |  |
| nitrocellulose | 8.87 | (dry) |
| ethyl acetate | 32.50 |  |
| butyl acetate | 28.35 |  |
| isopropyl alcohol | 11.52 |  |
| dibutyl phthalate | 6.50 |  |
| diacetone alcohol | 0.68 |  |
| citric acid | 0.02 |  |
| stearalkonium hectorite | 0.25 |  |
| stearalkonium bentonite | 0.75 |  |
|  | 100.00 |  |

EXAMPLE 4

| | WT. % |
|---|---|
| polyester resin | 5.60 |
| tosylamide epoxy resin | 4.96 |
| nitrocellulose | 8.87 (dry) |
| ethyl acetate | 32.50 |
| butyl acetate | 28.35 |
| isopropyl alcohol | 11.52 |
| triphenyl phosphate | 5.50 |
| dibutyl phthalate | 1.00 |
| diacetone alcohol | 0.68 |
| citric acid | 0.02 |
| stearalkonium hectorite | 0.25 |
| stearalkonium bentonite | 0.75 |
| | 100.00 |

The present invention will be further illustrated by way of the following comparative examples of conventional nail enamel compositions with examples of nail enamel compositions in accordance with the present invention.

EXAMPLE 5

| | WT. % |
|---|---|
| polyester resin | 8.40 |
| tosylamide epoxy resin | 4.96 |
| nitrocellulose 1/4/5–6 sec. | 8.87 (dry) |
| ethyl acetate | 30.00 |
| butyl acetate | 27.18 |
| isopropyl alcohol | 11.22 |
| triphenyl phosphate | 4.62 |
| 2,2,4-trimethyl-1,3-pentanediol diisobutyrate | .85 |
| dibutyl phthalate | .50 |
| camphor | .10 |
| diacetone alcohol | .68 |
| citric acid | 0.02 |
| stearalkonium hectorite | .25 |
| stearalkonium bentonite | .78 |
| D & C Red #6 barium Lake | .90 |
| D & C Red #7 calcium Lake | .35 |
| titanium dioxide | .32 |
| | 100.00 |

COMPARATIVE EXAMPLE 1

NAIL ENAMEL B

| | WT. % |
|---|---|
| nitrocellulose 1/4/1/2 sec. | 12.52 (dry) |
| toluene sulfonamide formaldehyde resin | 8.12 |
| butyl acetate | 22.79 |
| ethyl acetate | 18.74 |
| toluene | 19.69 |
| isopropyl alcohol | 5.72 |
| camphor | 1.10 |
| benzophenone 1 | 0.04 |
| dibutyl phthalate | 5.92 |
| diacetone alcohol | .84 |
| stearalkonium hectorite | .05 |
| stearalkonium bentonite | 1.24 |
| citric acid | 0.02 |
| polyester resin | 1.07 |
| toluene sulfonamide epoxy | 0.15 |
| titanium dioxide | .33 |
| D & C Red #6 barium Lake | .90 |
| D & C Red #7 calcium Lake | .76 |
| | 100.00 |

Twenty female panelists between the ages of twenty and sixty-five were selected for the study. All subjects had normal, healthy nails and were frequent users of nail enamel products. No pregnant or lactating women were included in the study. All twenty subjects completed the study.

Panelists cleansed their nails with acetone polish remover and washed their hands with Ivory Soap. For every two subjects, a bottle of Nail Enamel A (Example 5) and a bottle of Nail Enamel B (Comparative Example 1) were assigned. Each bottle was shaken prior to application. For subjects #1–#10, a licensed cosmetologist applied Nail Enamel A to alternate nails, starting with the right pinky, and Nail Enamel B was applied to the remaining alternate nails. For the remaining subjects (#11–#20), Nail Enamel B was applied to alternate nails, starting with the right pinky and Nail Enamel A was applied to the remaining alternate nails. After initial application, the nail enamel was allowed to dry for five minutes. A second coat was applied and allowed to dry for fifteen minutes.

After the second coat was applied, the Licensed Cosmetologist evaluated the nail enamel for application and appearance attributes. The criteria evaluated included thickness, opacity, evenness, dry time and gloss. Panelists were informed not to use any other nail enamel product, and in the event of a nail break, to minimally file to remove jagged edges. However, if a nail break interfered with the grading of nail enamel qualities, the broken nail and the same nail of the opposite hand were excluded from the evaluation.

All panelists returned on days 3, 5, 7, and 10 of the study for an evaluation of wear and gloss attributes. The gloss of the nail enamel was rated by the cosmetologist using a scale ranging from zero to four in whole number increments. The wear of the polish was rated using a scale that ranged from one to five in 0.5 point increments, corresponding with the amount of polish remaining on the nail tip at each evaluation day.

The nail enamel wear was evaluated by scoring the amount of polish remaining at the nail tips, where nail polish wear is typically most noticeable. On day 10, subject #13 exhibited wear that had the opposite orientation, wearing from the cuticle, but not from the tip. On day 3 of the study, subject #18 was not evaluated due to schedule conflict with work.

Total scores for initial application and appearance are listed in Table 1. Based on tabulation of individual scores for the Initial Application, Nail Enamel A and Nail Enamel B performed identically in thickness, opacity and evenness characteristics of application performance. In addition, Nail Enamel A and Nail Enamel B performed the same in Drying Time and Gloss parameters.

TABLE 1

Total Scores of Initial Application/Appearance
Total Scores
(N = 20)

| APPLICATION/ | Nail Enamel A | | | Nail Enamel B | | |
|---|---|---|---|---|---|---|
| INITIAL APPEARANCE | Total Score | Total Maximum Score | % of Maximum Score | Total Score | Total Maximum Score | % of Maximum Score |
| Thickness | 100 | 100 | 100% | 100 | 100 | 100% |
| Opacity | 100 | 100 | 100% | 100 | 100 | 100% |
| Evenness | 100 | 100 | 100% | 100 | 100 | 100% |
| Dry Time | 100 | 100 | 100% | 100 | 100 | 100% |
| Gloss | 100 | 100 | 100% | 100 | 100 | 100% |

The individual average scores for each subject for gloss evaluation at the examination days (Days 3, 5, 7 and 10) appear on Table II, and the individual average scores for wear evaluation at each examination appear on Table III. The overall average of the subjects' scores for each examination day are listed in the bottom rows of Tables II and III in columns corresponding to each examination day.

TABLE II

Average Scores for Gloss Evaluation

| Subject # | Nail Enamel A | | | | | | Nail Enamel B | | | | | | Relative % |
|---|---|---|---|---|---|---|---|---|---|---|---|---|---|
| | Day 3 | Day 5 | Day 7 | Day 10 | Average | % Max. Source | Day 3 | Day 5 | Day 7 | Day 10 | Average | % Max. Source | Difference (A − B) |
| 1 | 4.0 | 3.8 | 2.8 | 2.2 | 3.2 | 80 | 3.6 | 3.4 | 2.8 | 2.2 | 3.0 | 75 | 5 |
| 2 | 4.0 | 3.8 | 2.8 | 2.0 | 3.2 | 80 | 3.6 | 2.8 | 2.8 | 1.6 | 2.7 | 68 | 12 |
| 3 | 3.6 | 3.2 | 2.6 | 0.6 | 2.5 | 63 | 4.0 | 3.2 | 2.4 | 0.8 | 2.6 | 65 | 2 |
| 4 | 4.0 | 3.8 | 2.8 | 1.8 | 3.1 | 78 | 4.0 | 3.4 | 2.6 | 1.8 | 3.0 | 75 | 3 |
| 5 | 3.8 | 3.4 | 3.0 | 2.0 | 3.1 | 78 | 3.8 | 3.4 | 2.8 | 1.6 | 2.9 | 73 | 5 |
| 6 | 3.6 | 2.8 | 2.2 | 1.6 | 2.6 | 65 | 3.2 | 2.6 | 2.2 | 1.2 | 2.3 | 58 | 7 |
| 7 | 4.0 | 3.4 | 2.4 | 2.0 | 3.0 | 75 | 4.0 | 3.0 | 2.6 | 1.8 | 2.9 | 73 | 2 |
| 8 | 3.4 | 3.0 | 2.4 | 2.3 | 2.8 | 70 | 3.4 | 2.4 | 1.4 | 1.8 | 2.3 | 58 | 12 |
| 9 | 4.0 | 3.4 | 3.0 | 2.4 | 3.2 | 80 | 4.0 | 3.4 | 3.0 | 2.6 | 3.3 | 83 | 3 |
| 10 | 4.0 | 3.4 | 2.8 | 2.0 | 3.1 | 78 | 4.0 | 3.4 | 2.6 | 1.4 | 2.9 | 73 | 5 |
| 11 | 4.0 | 4.0 | 3.8 | 3.0 | 3.7 | 93 | 4.0 | 3.5 | 3.5 | 3.0 | 3.5 | 88 | 5 |
| 12 | 3.2 | 2.6 | 2.4 | 2.0 | 2.6 | 65 | 3.2 | 3.0 | 2.4 | 2.0 | 2.7 | 68 | −3 |
| 13 | 3.8 | 3.2 | 2.6 | 1.8 | 2.9 | 73 | 4.0 | 3.2 | 2.8 | 1.4 | 2.9 | 73 | 0 |
| 14 | 3.2 | 2.0 | 1.5 | 1.2 | 2.1 | 53 | 3.0 | 2.4 | 2.2 | 1.2 | 2.2 | 55 | −2 |
| 15 | 4.0 | 3.0 | 3.0 | 2.8 | 3.2 | 80 | 4.0 | 3.0 | 2.4 | 2.0 | 2.9 | 73 | 7 |
| 16 | 4.0 | 3.6 | 2.4 | 2.4 | 3.1 | 78 | 3.6 | 3.4 | 2.5 | 2.2 | 3.0 | 75 | 3 |
| 17 | 4.0 | 4.0 | 3.4 | 3.0 | 3.6 | 90 | 4.0 | 3.6 | 2.8 | 2.4 | 3.2 | 80 | 10 |
| 18 | ** | 3.0 | 3.0 | 2.4 | 2.8 | 70 | ** | 3.0 | 2.5 | 2.2 | 2.7 | 68 | 2 |
| 19 | 4.0 | 4.0 | 3.6 | 2.8 | 3.6 | 90 | 3.8 | 4.0 | 3.6 | 2.5 | 3.6 | 90 | 0 |
| 20 | 4.0 | 3.8 | 3.0 | 1.8 | 3.2 | 80 | 4.0 | 4.0 | 2.8 | 1.4 | 3.1 | 78 | 2 |
| Average | 3.8 | 3.4 | 2.8 | 2.1 | 3.0 | 76 | 3.7 | 3.2 | 2.7 | 1.9 | 2.9 | 72 | 4 |

**Day 3 evaluation was not made for subject #18

TABLE III

Average Scores for Wear Evaluation

| Subject # | Nail Enamel A | | | | | | Nail Enamel B | | | | | | Relative % |
|---|---|---|---|---|---|---|---|---|---|---|---|---|---|
| | Day 3 | Day 5 | Day 7 | Day 10 | Average | % Max. Source | Day 3 | Day 5 | Day 7 | Day 10 | Average | % Max. Source | Difference (A − B) |
| 1 | 4.8 | 4.6 | 4.5 | 4.4 | 4.6 | 92 | 5.0 | 4.6 | 4.4 | 4.2 | 4.6 | 92 | 0 |
| 2 | 4.6 | 4.3 | 4.3 | 4.0 | 4.3 | 86 | 4.6 | 4.4 | 4.3 | 3.6 | 4.2 | 84 | 2 |
| 3 | 4.9 | 4.3 | 3.6 | 2.6 | 3.9 | 78 | 4.5 | 3.4 | 2.5 | 1.9 | 3.1 | 62 | 16 |
| 4 | 4.7 | 4.5 | 4.5 | 4.0 | 4.4 | 88 | 4.9 | 4.6 | 4.4 | 3.4 | 4.3 | 86 | 2 |
| 5 | 4.5 | 4.2 | 3.9 | 3.2 | 4.0 | 80 | 4.3 | 3.6 | 3.3 | 2.7 | 3.5 | 70 | 10 |

TABLE III-continued

Average Scores for Wear Evaluation

| Subject # | Nail Enamel A | | | | | | Nail Enamel B | | | | | | Relative % |
| | Day 3 | Day 5 | Day 7 | Day 10 | Average | % Max. Source | Day 3 | Day 5 | Day 7 | Day 10 | Average | % Max. Source | Difference (A − B) |
| --- | --- | --- | --- | --- | --- | --- | --- | --- | --- | --- | --- | --- | --- |
| 6 | 4.8 | 4.7 | 4.6 | 4.1 | 4.6 | 92 | 4.9 | 4.6 | 4.3 | 3.5 | 4.3 | 86 | 6 |
| 7 | 4.5 | 4.1 | 3.5 | 3.1 | 3.9 | 78 | 4.0 | 3.3 | 2.8 | 2.0 | 3.0 | 60 | 18 |
| 8 | 4.7 | 4.6 | 4.5 | 4.1 | 4.5 | 90 | 4.5 | 4.6 | 4.5 | 3.6 | 4.4 | 88 | 2 |
| 9 | 5.0 | 4.8 | 4.6 | 4.2 | 4.7 | 94 | 4.8 | 4.1 | 3.5 | 3.2 | 4.0 | 80 | 14 |
| 10 | 4.7 | 4.1 | 3.8 | 3.3 | 4.0 | 80 | 4.4 | 3.7 | 3.2 | 2.6 | 3.5 | 70 | 10 |
| 11 | 4.8 | 4.7 | 4.6 | 4.3 | 4.6 | 92 | 4.5 | 4.1 | 3.8 | 3.4 | 4.0 | 80 | 12 |
| 12 | 5.0 | 4.6 | 4.5 | 4.4 | 4.6 | 92 | 5.0 | 4.6 | 4.4 | 3.7 | 4.4 | 88 | 4 |
| 13 | 4.9 | 4.7 | 4.5 | 4.4 | 4.6 | 92 | 4.9 | 4.7 | 4.5 | 2.7 | 4.2 | 84 | 8 |
| 14 | 4.6 | 4.5 | 4.3 | 3.7 | 4.3 | 86 | 4.4 | 4.0 | 3.4 | 3.1 | 3.7 | 74 | 12 |
| 15 | 4.6 | 4.5 | 4.4 | 4.4 | 4.5 | 90 | 4.9 | 4.5 | 4.4 | 4.1 | 4.5 | 90 | 0 |
| 16 | 4.4 | 4.4 | 4.1 | 3.9 | 4.2 | 84 | 4.6 | 4.3 | 4.1 | 3.8 | 4.2 | 84 | 0 |
| 17 | 4.2 | 4.1 | 3.9 | 3.7 | 4.0 | 80 | 4.3 | 4.0 | 3.5 | 3.3 | 3.9 | 78 | 2 |
| 18 | ** | 4.4 | 4.3 | 3.9 | 4.2 | 84 | ** | 4.2 | 4.0 | 3.3 | 3.3 | 76 | 8 |
| 19 | 4.6 | 4.3 | 4.3 | 4.1 | 4.2 | 84 | 4.7 | 4.3 | 4.1 | 3.6 | 4.2 | 84 | 0 |
| 20 | 4.7 | 4.4 | 4.0 | 3.9 | 4.3 | 86 | 4.7 | 4.4 | 3.9 | 3.4 | 4.1 | 82 | 4 |
| Average | 4.7 | 4.4 | 4.3 | 3.9 | 4.3 | 86 | 4.6 | 4.2 | 3.9 | 3.3 | 4.0 | 80 | 7 |

**Day 3 evaluation was not made for subject #18

The overall average gloss scores and wear scores of Nail Enamel A were higher than those calculated for Nail Enamel B at each examination interval. The Relative Percent Difference columns of Tables II and III list, on an individual subject basis, the percentage value by which Nail Enamel A out-performed Nail Enamel B. Subjects #2, #8, and #17 exhibited 10–12% more gloss on their nails polished with Nail Enamel A than on their nails polished with Nail Enamel B over the four evaluation days. Of the remaining seventeen subjects, fourteen subjects exhibited higher gloss (Range 2%–7%) on nails polished with Nail Enamel A. In subjects #3, #7 and #9, Nail Enamel A performed as much as 18% better than Nail Enamel B in wear performance scoring over the ten day study period. Thirteen of the remaining seventeen subjects exhibited 2–12% better wear with Nail Enamel A.

In addition to assigning scores for nail enamel wear, the extent and location of nail enamel wear was noted and is summarized as follows. Nail Enamel A-Day 3 no significant wear was observed; Day 5 no significant wear was observed; day 7 three subjects exhibited mild to moderate enamel wear at the sides of nails and/or the cuticle area; and day 10 two subjects (#19 and #20) exhibited mild enamel wear, each on one nail, two subjects (#3 and #13) each exhibited extreme enamel wear on one cuticle area and the sides of three nails.

Nail Enamel B-Day 3 no significant wear was observed; Day 5 subject #5 exhibited nail enamel wear near the cuticle are of all five nails; day 7 seven subjects exhibited nail enamel wear near the cuticle area and/or the sides of nails. In one of these subjects (#13), the wear in these areas was extreme; and day 10 four subjects exhibited extreme enamel wear near cuticle area and/or sides of nails.

Relative percent value for gloss and wear evaluations, obtained by summing the average daily scores of each subject at each examination interval and dividing by the potential maximum score, appear on Tables IV through VII.

TABLE IV

Relative Percent Values of Gloss Wear Evaluation Total Scores

| | Nail Enamel A | | | Nail Enamel B | | |
| | Total of Average Scores | Total Maximum Score | % of Maximum Score | Total of Average Scores | Total Maximum Score | % of Maximum Score |
| --- | --- | --- | --- | --- | --- | --- |
| GLOSS EVALUATION | 72.6 | 76 | 96% | 71.2 | 76 | 94% |
| WEAR EVALUATION | 89 | 95 | 94% | 88.2 | 95 | 93% |

TABLE V

Relative Percent Values of Gloss Wear Evaluation Total Scores

| | Nail Enamel A | | | Nail Enamel B | | |
| | Total of Average | Total Maximum | % of Maximum | Total of Average | Total Maximum | % of Maximum |

TABLE V-continued

|  | Scores | Score | Score | Scores | Score | Score |
|---|---|---|---|---|---|---|
| GLOSS EVALUATION | 67.2 | 80 | 84% | 64.1 | 80 | 80% |
| WEAR EVALUATION | 88.8 | 100 | 89% | 84 | 100 | 84% |

TABLE VI

Relative Percent Values of Gloss Wear Evaluation Total Scores

|  | Nail Enamel A | | | Nail Enamel B | | |
|---|---|---|---|---|---|---|
|  | Total of Average Scores | Total Maximum Score | % of Maximum Score | Total of Average Scores | Total Maximum Score | % of Maximum Score |
| GLOSS EVALUATION | 55.8 | 80 | 70% | 53.3 | 80 | 67% |
| WEAR EVALUATION | 85 | 100 | 85% | 77.9 | 100 | 78% |

TABLE VII

Relative Percent Values of Gloss Wear Evaluation Total Scores

|  | Nail Enamel A | | | Nail Enamel B | | |
|---|---|---|---|---|---|---|
|  | Total of Average Scores | Total Maximum Score | % of Maximum Score | Total of Average Scores | Total Maximum Score | % of Maximum Score |
| GLOSS EVALUATION | 42.1 | 80 | 53% | 37.4 | 80 | 47% |
| WEAR EVALUATION | 77.7 | 100 | 78% | 65.1 | 100 | 65% |

The relative percent value differences obtained at day 3 for gloss evaluation is 2% higher for Nail Enamel A compared to Nail Enamel B, and the relative percent obtained for nail enamel wear for Nail Enamel A is 1% higher than Nail Enamel B. On day 5, Nail Enamel A gloss is 4% higher than Nail Enamel B and wear is 5% higher. On day 7, there was a 3% difference in the gloss and a 7% difference in the wear of Nail Enamel A and Nail Enamel B, with Nail Enamel A scoring higher. On day 10, the difference in relative percent between Nail Enamel A and Nail Enamel B was in favor of Nail Enamel A by 6% for gloss evaluation and by 13% for wear evaluation. In the evaluation of gloss and wear attributes of the two nail enamel formulations, the scores obtained for Nail Enamel A at each evaluation interval (Days 3, 5, 7 and 10) were consistently higher.

EXAMPLE 6

NAIL ENAMEL B

|  | WT. % |
|---|---|
| polyester resin | 5.60 |
| tosylamide epoxy resin | 4.95 |
| nitrocellulose 1/4/5-6 sec. | 8.85 (dry) |
| ethyl acetate | 32.50 |
| butyl acetate | 26.50 |

-continued

|  | WT. % |
|---|---|
| isopropyl alcohol | 11.50 |
| triphenyl phosphate | 4.65 |
| 2,2,4-trimethyl-1,3-pentanediol diisobutyrate | 92 |
| dibutyl phthalate | .50 |
| camphor | .10 |
| diacetone alcohol | .68 |
| citric acid | 0.02 |
| stearalkonium hectorite | .25 |
| stearalkonium bentonite | .75 |
| titanium dioxide | 1.16 |
| iron oxides | .27 |
| D & C Red #7 | .20 |
| etocrylene | .50 |
| mica | .10 |
|  | 100.00 |

COMPARATIVE EXAMPLE 2

NAIL ENAMEL A

|  | WT. % |
|---|---|
| nitrocellulose 1/4/1/2 sec. | 12.57 (dry) |
| polyester resin | 8.10 |
| toluensulfonamide epoxy resin | .35 |
| ethyl acetate | 30.39 |
| butyl acetate | 16.75 |

-continued

| | WT. % |
|---|---|
| butyl alcohol | 1.71 |
| propyl acetate | 9.44 |
| isopropyl alcohol | 9.74 |
| dibutyl phthalate | 6.19 |
| camphor | 1.10 |
| diacetone alcohol | .66 |
| stearalkonium bentonite | 1.01 |
| stearalkonium hectorite | .02 |
| etocrylene | .50 |
| benzophenone 1 | 0.08 |
| citric acid | 0.02 |
| titanated mica | 0.12 |
| titanium dioxide | 1.00 |
| D & C Red #6 barium Lake | .05 |
| iron oxides | .10 |
| D & C Red #7 calcium Lake | .10 |
| | 100.00 |

Ten female panelists were selected for the study. All subjects had normal, healthy nails and were frequent users of nail products. No pregnant or lactating women were included in the study.

Panelists cleansed their nails with acetone polish remover and washed their hands with Ivory Soap. For every two subjects, a bottle of Nail Enamel A (Comparative Example 2) and a bottle of Nail Enamel B (Example 6) were assigned. Each bottle was shaken prior to application. For subjects #1–#10, a licensed cosmetologist applied Nail Enamel A to alternate nails, starting with the left pinky, and Nail Enamel B was applied to the remaining alternate nails (Subjects 1–5). Nail Enamel B was applied to alternate nails, starting with the left pinky and Nail Enamel A was applied to the remaining alternate nails (Subjects 6–10). After initial application, the nail enamel was allowed to dry for five minutes. A second coat was applied and allowed to dry for fifteen minutes.

After the second coat was applied, the Licensed Cosmetologist evaluated the nail enamel for application and appearance attributes. The criteria evaluated included thickness, opacity, evenness, dry time and gloss. Panelists were informed not to use any other nail product, and in the event of a nail break, to minimally file to remove jagged edges.

All panelists returned on day 3, day 7, and day 10 of the study for an evaluation of wear and gloss attributes. On day 3 of the study, subject number 3 was not evaluated due to an illness in the family. All ten subjects completed the study. Total scores for initial application and appearance are listed in Table I.

TABLE I

Total Scores of Initial Application/Appearance
Total Scores
(N = 10)

| APPLI-CATION/ | Nail Enamel A | | | Nail Enamel B | | |
|---|---|---|---|---|---|---|
| INITIAL APPEAR-ANCE | Total Score | Total Maximum Score | % of Maximum Score | Total Score | Total Maximum Score | % of Maximum Score |
| Thickness | 50 | 50 | 100% | 40 | 50 | 80% |
| Opacity | 50 | 50 | 100% | 40 | 50 | 80% |
| Evenness | 50 | 50 | 100% | 40 | 50 | 80% |

TABLE I-continued

Total Scores of Initial Application/Appearance
Total Scores
(N = 10)

| APPLI-CATION/ | Nail Enamel A | | | Nail Enamel B | | |
|---|---|---|---|---|---|---|
| INITIAL APPEAR-ANCE | Total Score | Total Maximum Score | % of Maximum Score | Total Score | Total Maximum Score | % of Maximum Score |
| Dry Time | 49 | 50 | 98% | 49 | 50 | 98% |
| Gloss | 50 | 50 | 100% | 50 | 50 | 100% |

Individual average scores for gloss evaluation for the three evaluations (Days 3, 7 and 10) appear on Table II.

TABLE II

Individual Average Scores of Gloss Evaluation
(Day 3, 7, 10)

| Subject Number | Nail Enamel A | Nail Enamel B |
|---|---|---|
| 1 | 2.5 | 2.9 |
| 2 | 2.9 | 3.1 |
| 3* | 2.3 | 2.9 |
| 4 | 2.5 | 2.7 |
| 5 | 3.3 | 3.5 |
| 6 | 3.1 | 3.2 |
| 7 | 2.7 | 2.5 |
| 8 | 2.7 | 2.9 |
| 9 | 2.9 | 3.2 |
| 10 | 2.7 | 2.5 |

*Subject #3 scores are based on two (2) evaluations (no evaluation day 3)

Individual average scores for wear evaluation for the three evaluations appear on Table III.

TABLE III

Individual Average Scores of Wear Evaluation
Day (3, 7, 10)

| Subject Number | Nail Enamel A | Nail Enamel B |
|---|---|---|
| 1 | 3.5 | 3.8 |
| 2 | 4.2 | 4.3 |
| 3* | 2.7 | 3.8 |
| 4 | 3.9 | 4.4 |
| 5 | 4.4 | 4.5 |
| 6 | 4.3 | 4.5 |
| 7 | 4.4 | 4.7 |
| 8 | 4.3 | 4.4 |
| 9 | 4.3 | 4.2 |
| 10 | 3.9 | 4.1 |

*Subject #3 scores are based on two (2) evaluations (no evaluation day 3)

Total percentage scores for gloss and wear evaluations appear on Table IV.

TABLE IV

Total Percentage Scores of Gloss and Wear Evaluation
Total Scores

|  | Nail Enamel A | | | Nail Enamel B | | |
| --- | --- | --- | --- | --- | --- | --- |
|  | Total of Average Scores | Total Maximum Score | % of Maximum Score | Total of Average Scores | Total Maximum Score | % of Maximum Score |
| GLOSS EVALUATION | 27.6 | 40 | 70% | 29.4 | 40 | 74% |
| WEAR EVALUATION | 39.9 | 50 | 80% | 42.7 | 50 | 85% |

Based on a tabulation of individual scores for the Initial Application, Nail Enamel A performed better than Nail Enamel B in thickness, opacity and evenness parameters of application performance. Nail Enamel A and Nail Enamel B performed the same in Drying Time and Gloss parameters (Table I).

Based on a tabulation of individual average Gloss Evaluations, Nail Enamel B performed better than Nail Enamel A in eight of ten subjects (Table II). No differences between Products were found on day 3 and day 7. On day 10, Nail Enamel B was found to be significantly better than Nail Enamel A.

Individual average scores for the Wear Evaluations indicate that Nail Enamel B performed better than Nail Enamel A in nine of ten subjects. (Table III). Average scores for days 3, 7 and 10 were analyzed for significant differences in wear utilizing a Sign Test for significance. No differences between formulations were found on day 3. On day 7 and day 10, Nail Enamel B was found to be significantly better than Nail Enamel A. Based on a total percentage of scores for Gloss and Wear Evaluations, Nail Enamel B performed better than Nail Enamel A (Table IV).

Although the invention herein has been described with reference to particular embodiments, it is to be understood that the embodiments are merely illustrative of the principles and application of the present invention. It is therefore to be understood that numerous modifications may be made to the embodiments and that other arrangements may be devised without departing from the spirit and scope of the present invention as defined by the claims.

What is claimed is:

1. A nail enamel composition comprising nitrocellulose as a film forming polymer, a mixture of a polyester resin and a sulfonamide epoxy resin as a film forming resin present in an amount greater than an amount of said film forming polymer, a solvent and a plasticizer.

2. The nail enamel composition of claim 1, wherein said nitrocellulose includes at least one compound selected from the group consisting of nitrocellulose RS ⅛ sec., nitrocellulose RS ¼ sec., nitrocellulose RS ½ sec., nitrocellulose RS 60–80 sec. and nitrocellulose RS 5–6 sec. and mixtures thereof.

3. The nail enamel composition of claim 1, wherein said film forming polymer is present in an amount less than about 10% and said film forming resin is present in an amount greater than about 10%.

4. The nail enamel composition of claim 1, wherein said plasticizer comprises 2, 2, 4-trimethyl-1, 3-pentanediol diisobutyrate .

5. The nail enamel composition of claim 1, wherein said film forming polymer is present in the range of about 5 to 20% by weight, said film forming resin is present in the range of about 10 to 25% by weight, said solvent is present in the range of about 55 to 80% by weight, and said plasticizer is present in the range of about 3 to 10% by weight.

6. The nail enamel composition of claim 1, wherein said film forming polymer is present in the range of about 6 to 9% by weight, said film forming resin is present in the range of about 10 to 15% by weight, said solvent is present in the range of about 60 to 75% by weight, and said plasticizer is present in the range of about 4 to 8% by weight.

7. The nail enamel composition of claim 1, wherein said composition further includes a thixotropic agent.

8. The nail enamel composition of claim 1, wherein said film forming resin comprises formaldehyde free resins.

9. The nail enamel composition of claim 1, wherein said solvent comprises one or more toluene free solvents and mixture thereof.

10. A nail enamel composition comprising nitrocellulose as a film forming polymer, a mixture of a polyester resin and a sulfonamide epoxy resin as a film forming resin present in an amount greater than an amount of said film forming polymer, a solvent and a plasticizer, wherein said composition is free of mica in the form of a leaf and hydrocarbon based solvents.

11. The nail enamel composition of claim 10, wherein said nitrocellulose includes at least one compound selected from the group consisting of nitrocellulose RS ⅛ sec., nitrocellulose RS ¼ sec., nitrocellulose RS ½ sec., nitrocellulose RS 60–80 sec. nitrocellulose RS 5–6 sec. and mixtures thereof.

12. The nail enamel composition of claim 10, wherein said film forming polymer is present in an amount less than about 10% and said film forming resin is present in an amount greater than about 10%.

13. The nail enamel composition of claim 10, wherein said plasticizer comprises 2, 2, 4-trimethyl-1, 3-pentanediol diisobutyrate .

14. The nail enamel composition of claim 10, wherein said film forming polymer is present in the range of about 5 to 20% by weight, said film forming resin is present in the range of about 10 to 25% by weight, said solvent is present in the range of about 55 to 80% by weight, and said plasticizer is present in the range of about 3 to 10% by weight.

15. The nail enamel composition of claim 10, wherein said film forming polymer is present in the range of about 6 to 9% by weight, said film forming resin is present in the range of about 10 to 15% by weight, said solvent is present in the range of about 60 to 75% by weight, and said plasticizer is present in the range of about 4 to 8% by weight.

16. The nail enamel composition of claim 10, wherein said composition further includes a thixotropic agent and at least one pigment.

17. The nail enamel composition of claim 10, wherein said film forming resin comprises formaldehyde free resins.

18. The nail enamel composition of claim 10, wherein said solvent comprises one or more toluene free solvents and mixture thereof.

19. A nail enamel composition comprising nitrocellulose as a film forming polymer, a mixture of a polyester resin and a sulfonamide epoxy resin as a film forming resin, said film forming resin present in an amount greater than an amount of said film forming polymer, a solvent, a plasticizer and a colorant.

20. The nail enamel composition of claim 19, wherein said nitrocellulose includes at least one compound selected from the group consisting of nitrocellulose RS ⅛ sec., nitrocellulose RS ¼ sec., nitrocellulose RS ½ sec., nitrocellulose RS 60–80 sec., nitrocellulose RS 5–6 sec. and mixtures thereof.

21. The nail enamel composition of claim 19, therein said film forming resin comprises formaldehyde free resins and said solvent comprises one or more toluene free solvents and mixtures thereof.

22. The nail enamel composition of claim 19, wherein said film forming polymer is present in an amount less than about 10% and said film forming resin is present in an amount greater than about 10%.

23. The nail enamel composition of claim 19, wherein said plasticizer comprises 2, 2, 4-trimethyl-1, 3-pentanediol diisobutyrate.

24. The nail enamel composition of claim 19, wherein said film forming polymer is present in the range of about 5 to 20% by weight, said film forming resin is present in the range of about 10 to 25% by weight, said solvent is present in the range of about 55 to 80% by weight, and said plasticizer is present in the range of about 3 to 10% by weight.

25. The nail enamel composition of claim 19, wherein said film forming polymer is present in the range of about 6 to 9% by weight, said film forming resin is present in the range of about 10 to 15% by weight, said solvent is present in the range of about 60 to 75% by weight, and said plasticizer is present in the range of about 4 to 8% by weight.

26. The nail enamel composition of claim 19, wherein said composition further includes a thixotropic agent and at least one pigment as said colorant.

27. The nail enamel composition of claim 19, wherein said film forming resin comprises formaldehyde free resins.

28. The nail enamel composition of claim 19, wherein said solvent comprises one or more toluene free solvents and mixture thereof.

29. The nail enamel composition of claim 19, wherein said solvents are selected from the group consisting of ethyl acetate, butyl acetate, isopropyl alcohol and mixtures thereof.

30. The nail enamel composition of claim 19, wherein said sulfonamide epoxy resin comprises tosylamide epoxy resin.

31. A toluene formaldehyde free nail enamel composition comprising about 5 to 20% by weight nitrocellulose, about 10 to 25% by weight of one or more formaldehyde free film forming resins comprising a mixture of a polyester resin and a sulfonamide epoxy resin, said film forming resin present in an amount greater than the amount of said nitrocellulose, a solvent and a plasticizer, and optionally a thixotropic agent and at least one pigment.

32. The nail enamel composition of claim 31, wherein said plasticizer comprises 2, 2, 4-trimethyl-1, 3-pentanediol diisobutyrate.

33. The nail enamel composition of claim 31, wherein said solvents are selected from the group consisting of ethyl acetate, butyl acetate, isopropyl alcohol and mixtures thereof.

34. The nail enamel composition of claim 33, wherein said sulfonamide epoxy resin comprises tosylamide epoxy resin.

35. The nail enamel composition of claim 1, wherein said composition is acetone free.

36. The nail enamel composition of claim 10, wherein said composition is acetone free.

37. The nail enamel composition of claim 19, wherein said composition is acetone free.

38. The nail enamel composition of claim 31, wherein said composition is acetone free.

39. The nail enamel composition of claim 1, wherein said sulfonamide epoxy resin comprises tosylamide epoxy resin.

40. The nail enamel composition of claim 12, whereon said sulfonamide epoxy resin comprises tosylamide epoxy resin.

* * * * *

UNITED STATES PATENT AND TRADEMARK OFFICE
CERTIFICATE OF CORRECTION

PATENT NO. : 5,863,523
DATED : January 26, 1999
INVENTOR(S) : Socci et al.

It is certified that error appears in the above-identified patent and that said Letters Patent is hereby corrected as shown below:

Column 7, after "Example 5", insert a heading --Nail Enamel A--.
Columns 9 and 10, Table II, Subject #14, under "Day 7" "1.5" should read --1.8--.
Columns 9 and 10, Table II, Subject #16, under "Day 7" "2.5" should read --2.8--.
Columns 9 and 10, Table II, Subject #18, under "Day 7" "2.5" should read --2.8--.
Columns 9 and 10, Table II, Subject #19, under "Day 7" "2.5" should read --2.8--.
Columns 11 and 12, Table III, Subject #7, under "Day 7" "3.5" should read --3.8--.
Columns 11 and 12, Table III, Subject #8, under "Day 3" "4.5" should read --4.8--.
Columns 11 and 12, Table III, Subject #9, under "Day 7" "3.5" should read --3.8--.
Columns 11 and 12, Table III, Subject #17, under "Day 7" "3.5" should read --3.8--.
Columns 11 and 12, Table III, Subject #18, under "Day 7" "3.3" should read --3.8--.
Column 12, under "Table IV", in the heading after "Gloss" insert --and--.
Column 12, under "Table V", in the heading after "Gloss" insert --and--.
Column 12, under "Table VI", in the heading after "Gloss" insert --and--.
Column 12, under "Table VII", in the heading after "Gloss" insert --and--.
Column 19, line 13, "therein" should read --wherein--.
Column 38, line 30, "12" should read --10--.
Column 38, line 30, "whereon" should read --wherein--.

Signed and Sealed this

Thirteenth Day of July, 1999

Attest:

Attesting Officer

Q. TODD DICKINSON

Acting Commissioner of Patents and Trademarks